United States Patent [19]

Weeks

[11] Plant 5,098

[45] Sep. 6, 1983

[54] ROSE PLANT

[76] Inventor: O. L. Weeks, 926 W. Philadelphia, Ontario, Calif. 91761

[21] Appl. No.: 329,241

[22] Filed: Dec. 10, 1981

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Vincent G. Gioia

[57] ABSTRACT

A new hybrid tea rose variety of Indian orange and pale yellow coloring.

1 Drawing Figure

The present invention relates to a new and distinct variety of rose plant of the hybrid tea rose class, named Orange Parfait which was originated by my crossing as seed and pollen parents two unnamed, unpatented seedlings of my creation.

The seed parent is somewhat like Tiffany and has some marked greenish yellow shadings at petal base and is a blend of pink and yellow shading in contrast to my new rose which is a distinct bi-color of pale yellowish petal undersurface and Indian orange petal top surface. Foliage of the new rose is heavier and more waxy than the seed parent.

The pollen parent is a red rose, in contrast to the bicolored new rose, and grows taller and with heavier foliage.

The new rose is a high centered Indian orange and pale yellow bicolor attractively displayed against abundant dark green, leathery foliage blooming singly on sturdy stems and becoming ruffled at maturity.

Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "160B" is plate 160B of The Royal Horticultural Society Colour Chart.

Parentage: Seedling.

*Seed parent.*—Unnamed, unpatented seedling.

*Pollen parent.*—Unnamed, unpatented seedling.

Class: Hybrid Tea.

The following observations are made of specimens grown outdoors in San Bernardino County, Calif., during the month of August.

FLOWER

Blooming habit: Recurrent.

A. Bud (1) *Size.*—Medium.

(2) *Form.*—Ovoid to moderately pointed.

(3) *Color.*—When sepals first divide, buds display pale greenish yellow 160B at base (petal undersurface) blending upward to reddish orange. As outer petals begin to unfurl the outside petal (undersurface) is greenish yellow at base (160B) blending upward with some 170D coloring indicated. The edge of the petal (undersurface) as petals of bud unfurl is Indian orange 32A.

(4) *Sepals.*—Long, medium width, extending to top of unopened bud. Two with straight edges. Three with fringed edges.

(5) *Peduncle.*—Length — Medium. Aspect — Straight. Strength — Erect, heavy. Color — Yellowish green.

B. Bloom:

(1) *Size.*—Average size when fully expanded — about 4½ to 5 inches.

(2) *Borne.*—Singly.

(3) *Form.*—High centered at first, at first petals loosely rolled outward quilling to points and becoming ruffled at maturity.

(4) *Petalage.*—Number of petals under normal conditions — about 40 to 45.

(5) *Color.*—Petal undersurface is 160A at the base lightening upward but including some blending of 32A with some veining indicated. Petal top surface is bright 160A at the base (point of attachment) only but predominantly Indian Orange 32A at ¼ to ⅓ open stage. Opening flower is distinctly bi-color with pale yellowish petal undersurface and orange colored petal top surface. At full open bloom stage petal top surface coloring lightens to 39B to 39C and predominates since petal undersurface coloring is not visible from above.

C. Petals:

(1) *Texture.*—Thick, heavy.

(2) *Appearance.*—Inside and outside satiny.

(3) *Form.*—Large globular, slightly ovoid.

(4) *Arrangement.*—Very double, imbricated, no stamens showing.

(5) *Petaloids in center.*—Numerous.

(6) *Persistence.*—Drop off cleanly.

(7) *Fragrance.*—Very slight tea.

(8) *Lasting quality.*—Long lasting on plant.

REPRODUCTIVE ORGANS

A. Stamens, filaments and anthers:

(1) *Arrangement.*—Regularly arranged tucked in calyx.

(2) *Color.*—Reddish yellow.

B. Pollen:
*Color.*—Golden yellow.
C. Styles: Uneven, short, bunched.
D. Stigmas:
*Color.*—Yellow.
E. Hips: None observed.

PLANT

A. Form: Upright, compact.
B. Growth: Vigorous, irregular branching.
*Height attained.*—About 4½ to 5 feet.
C. Foliage: Compound 3 to 5 leaflets.
(1) *Size.*—Medium to large.
(2) *Quantity.*—Abundant.
(3) *Color.*—New foliage: Upper side — Purplish becoming dark green. Under side — Reddish green. Old foliage: Leathery, dark green.
(4) *Shape.*—Oval.
(5) *Texture.*—Upper side is waxy, leathery and under side is dull.
(6) *Edge.*—Serrated.
(7) *Serration.*—Simple.
(8) *Leaf stem.*—Color — near to 138B. Under side — near 138B to 138C.
(9) *Stipules.*—Long, bearded.

(10) *Resistance to disease.*—Mildew — Average. Rust — Average.
D. Wood:
(1) *New wood.*—Color — near 138B. Bark — Dull, numerous small prickles.
(2) *Old Wood.*—Color — near 138A. Bark — numerous small prickles.
E. Thorns:
(1) *Thorns.*—Quantity (main stalk) — ordinary but with prickles between thorns. On laterals from stalk — few. Form — long, narrow, oval base, pointed sharply downward. Length — long. Color — reddish at base to yellowish green at point. Position — regular.
(2) *Prickles.*—Numerous.
F. Winter hardiness: Average winter hardiness.

I claim:

1. A new and distinct variety of rose plant of the hybrid tea class, substantially as shown and described, characterized particularly by high centered Indian Orange and pale yellow bicolored flowers borne singly on strong stems becoming ruffled at maturity and abundant, dark green leathery foliage.

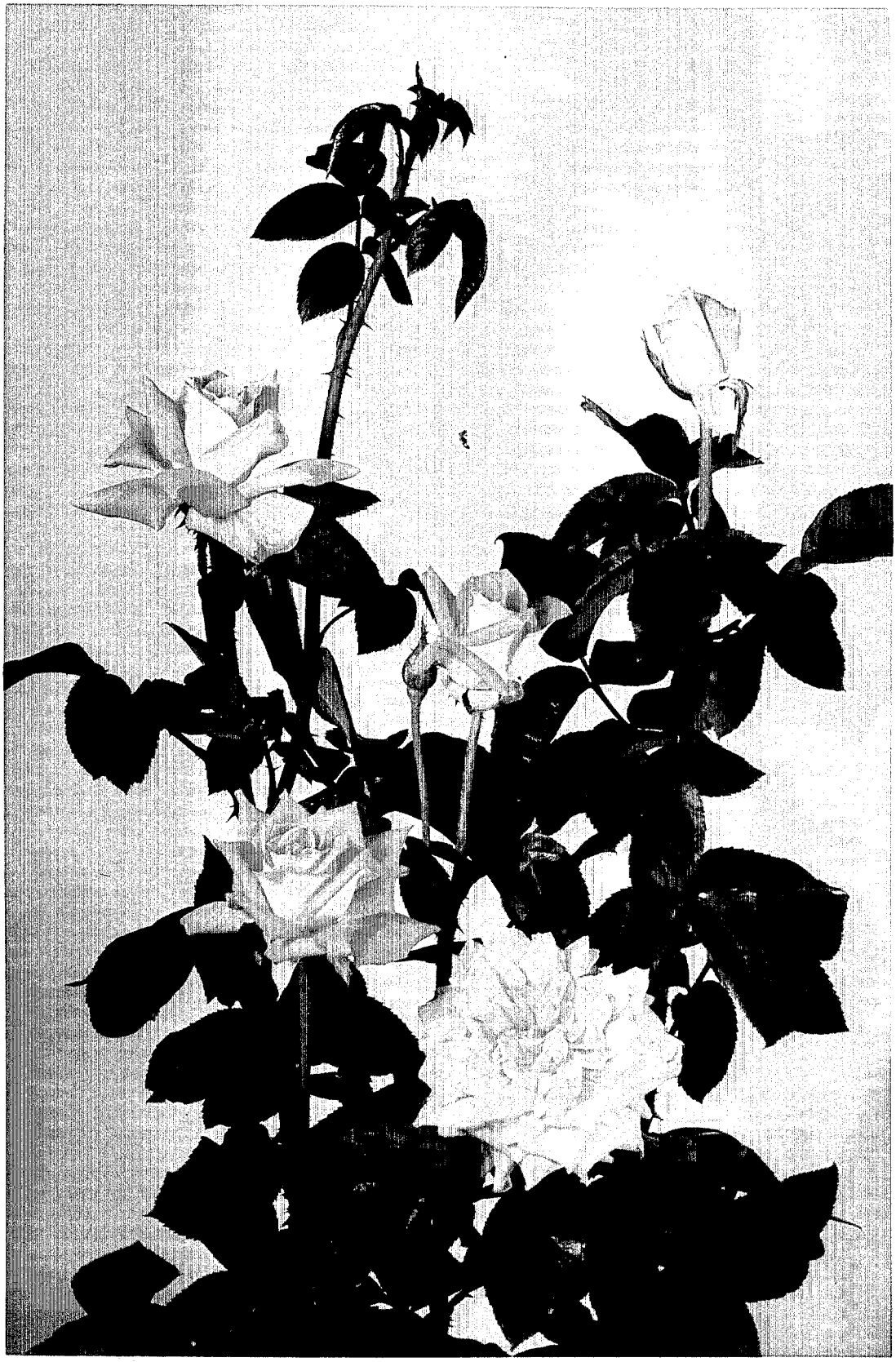

* * * * *